(12) United States Patent
Wei

(10) Patent No.: US 10,478,463 B2
(45) Date of Patent: Nov. 19, 2019

(54) EXTERNAL-USE MEDICAMENT FOR CLEANING AND CARE OF THE OVARIES, VAGINA, AND VULVA

(71) Applicant: Jianxue Wei, Xi'an (CN)

(72) Inventor: Jianxue Wei, Xi'an (CN)

(*) Notice: Subject to any disclaimer, the term of this patent is extended or adjusted under 35 U.S.C. 154(b) by 617 days.

(21) Appl. No.: 14/783,208

(22) PCT Filed: Feb. 21, 2014

(86) PCT No.: PCT/CN2014/072376
§ 371 (c)(1),
(2) Date: Oct. 8, 2015

(87) PCT Pub. No.: WO2014/166317
PCT Pub. Date: Oct. 16, 2014

(65) Prior Publication Data
US 2016/0051595 A1 Feb. 25, 2016

Related U.S. Application Data

(63) Continuation-in-part of application No. PCT/CN2014/072376, filed on Feb. 21, 2014.

(30) Foreign Application Priority Data

Apr. 8, 2013 (CN) .......................... 2013 1 0120184

(51) Int. Cl.
| | |
|---|---|
| *A61K 35/644* | (2015.01) |
| *A61K 36/9066* | (2006.01) |
| *A61K 36/534* | (2006.01) |
| *A61K 9/00* | (2006.01) |
| *A61K 36/906* | (2006.01) |
| *A61K 9/70* | (2006.01) |

(52) U.S. Cl.
CPC .......... *A61K 35/644* (2013.01); *A61K 9/0034* (2013.01); *A61K 36/534* (2013.01); *A61K 36/906* (2013.01)

(58) Field of Classification Search
CPC .............. A61K 2300/00; A61K 35/644; A61K 36/534; A61K 36/9066; A61K 2236/00; A61K 9/0034
See application file for complete search history.

(56) References Cited

U.S. PATENT DOCUMENTS

2003/0206943 A1* 11/2003 Hammons ......... A61F 13/51305
424/443

FOREIGN PATENT DOCUMENTS

| CN | 1762388 A | 4/2006 | |
|---|---|---|---|
| CN | 1840155 A | 10/2006 | |
| CN | 101095895 A | * 1/2008 | |
| CN | 101095895 A | 1/2008 | |
| CN | 201529207 U | 7/2010 | |
| CN | 103386076 A | 11/2013 | |
| CN | 104096163 A | * 10/2014 | .......... A61K 9/0034 |
| WO | 0111971 A1 | 2/2001 | |

OTHER PUBLICATIONS

Ullah et al. "Evaluation of antinociceptive, in-vivo & in-vitro anti-inflammatory activity of ethanolic extract of Curcuma zedoaria rhizome" BMC Complementary and Alternative Medicine 2014, 14:346 (12 pages). (Year: 2014).*
International Search Report issued in corresponding application No. PCT/CN2014/072376, dated May 30, 2014.
Office Action issued in corresponding application No. CN 201310120184.0, dated May 25, 2017.
Notification of Allowance issued in corresponding application No. CN 201310120184.0, dated Nov. 24, 2017.
Search Report issued in corresponding application No. CN 201310120184.0, dated May 16, 2017.

* cited by examiner

*Primary Examiner* — Aaron J Kosar
(74) *Attorney, Agent, or Firm* — Carter, DeLuca & Farrell LLP

(57) ABSTRACT

An external-use agent for cleaning and caring ovaries, vagina and vulva, which is produced by medical raw materials consisting of propolis extract, zedoary oil, and mint leaf filtrate is provided. On the basis of different properties of each natural Chinese herbal material, using supercritical $CO_2$ technology, separation and extraction, and low-temperature centrifugation are carried out respectively, and they are processed for preparation in a proportion, and then the membrane separation is performed, so that a spraying agent or a caring product is manufactured. It may be used alone in a female reproductive system for preventing the repeated infection and for achieving vulval bacteriostatic or antibacterial purposes and cleaning and deodorizing the vagina, eliminating vulval pruritus, and refreshing and moisturizing vulva and vagina etc., with good cleaning and caring functions and achieving a significant effect.

5 Claims, No Drawings

EXTERNAL-USE MEDICAMENT FOR CLEANING AND CARE OF THE OVARIES, VAGINA, AND VULVA

TECHNICAL FIELD

The present invention belongs to the technical field of medical preparation, relates to an external-use agent for caring ovaries, vagina and vulva and keeping the internal and external environment of a female reproductive system clean, with the external-use agent manufactured using natural Chinese herbal material as raw materials. The present invention also relates to a manufacturing method of the external-use agent.

BACKGROUND ART

Over the past decade, gynecological vaginal diseases have become common and frequently-occurring diseases seriously harming women's health. According to related statistics, currently 80% or more of the female adult population in the world are suffering from a gynecological vaginal disease. On average, a woman uses a gynecological medicament 5 times per year. And among many gynecological disorders affecting women's health, a vaginal disease caused by gynecological uncleanness is the female disease occurring most frequently. In daily life, although many women are aware of the importance of keeping the vagina clean and also able to wash the vulva or change an underwear frequently, they often use, due to being confined to the living environment and other factors, a washing machine to rinse clothes and then dry them, but seldom conduct disinfection or sunbathing for the clothes especially underwear. Such unclean underwear causes a vaginal infection disease, which also is the first major disease harming women's health.

A gynecological vaginal disease is a vaginal cell mucosal tissue injuring disease of women caused by exogenous viruses, pathogenic bacteria infection etc. Because women's vaginal epidermal tissue cells are a class of cells having secretion capability, they have many functions of secreting self-cleaning substances, secreting female hormones, secreting endocrine hormone, secreting immune components and secreting lubricating fluid etc. But in the past, during the treatment of such diseases, frequently because the medicaments used have a certain irritation and more frequently because medical preparations cannot be absorbed by vaginal mucosa cells, medicament residue is left, which causes secondary pollution to the vagina, resulting in attenuation or decrease in the secretion function of vaginal mucosa cells, leading to that women have prematurely phenomena of dryness and coarseness, decrease in the secretion function of vaginal cells, difficulties in sexual life and premature menopause and the like.

Currently, there are many medicaments used in the art for prevention and treatment of gynecological vaginal diseases. Especially, some Chinese and Western medicine formulations have also created an advantage of having quite unique efficacy in clinical practice. But because of the high incidence of gynecological vaginal diseases and because the pathological mechanism is relatively complex, the existing medical preparations do not fully meet clinical and market requirements in efficacy. Although some chemicals have anti-inflammatory and antibacterial effects, the problem of reducing irritation to the vaginal mucosa cells has not been taken into account. Thus, they have side effects, obviously irritating vaginal mucosal cells. Although some lotions and emulsions clean the vagina, the use for long-term will flush out a large number of secretions of the vaginal mucosal cells, which not only causes the phenomenon of gynecological dryness and coarseness, but also more easily causes the vagina to be infected by bacteria and viruses due to loss of protection effect of secretion from the mucous membranes. In addition, regarding the formulation of medicaments, today in domestic and overseas, in addition to lotions and emulsions, medicaments for treatment of gynecological vaginal diseases are mainly in form of tablets, hard gelatin capsules, and suppositories. The medicaments of these formulations contain relatively high content of impurities, which cause huge damage to secretory function of the vaginal mucosal cells. In summary, in this technical field, there would be a trend for gynecological vaginal administration in the future to develop a gynecological product, which can effectively protect, for reducing the use frequency of gynecological medicaments, the clean environment of vagina, which is also an important indicator of delaying the aging of vaginal cells.

DETAILED DESCRIPTION

The present invention has the object to solve the problems existing in the prior art, and thus provides an external-use agent for cleaning and caring ovaries, vagina and vulva, manufactured using natural Chinese herbal material as raw materials, which can prevent repeated infection of the ovaries, vagina, cervix, has cleaning and antibacterial effects on the vagina and vulva, and deodorize the gynecological vagina. The present invention also provides a manufacturing process for the preparation of the external-use agent.

The technical solution of preparation of the external-use agent of the present invention is obtained by the inventor, on the basis of a traditional Chinese medicine concept that a treatment is made dialectically as well as experiments of modern medicine, through a careful summarization and preparation. The external-use agent is a pure natural Chinese herbal care product manufactured on the basis of a pharmacological data analysis on selected medicaments as well as the practical experience and knowledge about its cleaning effect on ovaries, vagina and vulva using modern biotechnological manufacturing means. The traditional Chinese medical product is manufactured using the following raw materials, as active ingredients, based on parts by weight:

Propolis extract 1~10 parts,
Zedoary oil 5~10 parts, and
Mint leaf filtrate 50~100 parts.

The method for preparing the external-use agent comprises the following process steps of:

1. preparing the propolis extract, including: loading raw propolis into a $CO_2$ extraction tank and circularly adding $CO_2$ liquid to perform extraction with an extraction temperature of 15~30° C., an extraction pressure of 8~10 MPa, and extraction time of 1 to 2 hours, to obtain the propolis extract, the propolis content of which is 1% to 3% of amount of the raw propolis;

2. preparing the zedoary oil, including: directly loading zedoary seeds into a $CO_2$ extraction tank and circularly adding $CO_2$ liquid to perform extraction with a extraction temperature of 20~30° C., a extraction pressure of 2~7 MPa, and extraction time of 1~2 hours, to obtain zedoary oil extract containing plant zedoary ketone ingredient;

3. preparing the mint leaf filtrate, including: mixing fresh mint leafs with pure water in a weight ratio of 1:2~3, mechanically breaking into pieces, then adding into medical ethanol of 0.1 to 0.2 times in weight, soaking them for 10~15 hours, and filtrating with a 200 mesh screen to remove precipitate to obtain the mint leaf filtrate;

4. dissolving the above-mentioned propolis extract, zedoary extract (zedoary oil) and mint leaf filtrate, in accordance with requirement of the formula composition, into ethanol solution of 0.1 to 0.3 times by weight of the active ingredients and mixing them, and then removing, by means of freezing and centrifugation, the precipitate under the following conditions: a frozen temperature of 0° C.~4° C. and a centrifugal rotation speed of 3000 rpm~4000 rpm, duration of 10~20 minutes, and then separating the centrifugate by an acoustic membrane separator to obtain a medical liquid with a molecular weight less than 10000D, and then bottling or bagging the medical liquid to obtain the external-use agent of the present invention for cleaning and caring ovaries, vagina and vulva.

The external-use agent manufactured using the above medical raw materials fully reflect the traditional Chinese medical concept that a treatment is made dialectically: "radically reforming", "treating both manifestation and root cause of disease". The pharmacological effects of each component in the prescription are as follows:

Pharmacological effects of the propolis: the propolis extract is a propolis substance obtained using a supercritical $CO_2$ extraction process, the main components thereof is natural plant flavones, the propolis flavones component is a natural broad-spectrum antibacterial agents, antioxidants; the propolis can significantly enhance the immune function of cells and organism, has a stronger bactericidal and bacteriostatic power, plays an effective anti-bacterial anti-inflammatory role, and enhances the human body's resistance to disease and self-healing power; antioxidant capacity of the propolis can effectively stabilize and eliminate free radicals, protect cell membranes and enhance cell viability, and promote the self-secretory function of cells.

Pharmacological effects of the zedoary oil: zedoary oil has the functions of promoting Qi to activate blood, removing food retention and relieving pain, activating blood circulation to dissipate blood stasis, removing necrotic tissue and promoting granulation, enhancing the immune function of organisms, playing a synergistic bactericidal effect together with propolis, as well as promoting wound healing, having a therapeutic effect on RSV-infected cells, and having stronger inhibitory on virus propagation and antibacterial effect.

Pharmacological effects of the mint: mint has the functions of anti-inflammatory and relieving pain, antipruritic effect and detoxification, dispelling wind-heat (eliminating uncomfortable symptoms caused by suffering cold and heat), promoting eruption and antipruritic effect, and eliminating cutaneous pruritus.

Results of clinical use of the medical product according to the present invention show that the medical product has the following advantages:

1. the product according to the present invention is manufactured using selected natural materials according to the technical requirements of biological preparation for preventing repeated gynecological infection and protecting the clean environment of vagina and vulva, and the product contains propolis plant flavones, curzerenone, peppermint camphor, and menthol, without hybrid synthetic medicaments and allergen substances, producing no irritation to the vulva and no toxic side effect on vulvar tissue cell metabolism, thus the product is nontoxic and not harmful to human body;

2. the product according to the present invention can be used alone as a gynecological cleaning product, having the effect of deodorizing the vagina and bacteriostatic, antibacterial, antiviral effects;

3. the product according to the present invention can be used alone as a care product for a female reproductive system, having the effects of protecting and curing the ovaries; and 4. the product according to the present invention has good assistant and care effects on rehabilitation of gynecological diseases, and in addition, significantly relieves vulval itching occurring in the middle aged and old people.

In an implementation, the external-use agent can be used for producing a variety of products for protecting, cleaning and caring the ovaries, vagina and vulva, such as female vulval spraying agent, female medical vulval pads etc. The Female vulval spraying agent is manufactured using the external agent and purified water or alcohol being compounded in the proportion of 1:5~10. The preparation method of female medical vulval pads comprises steps of: dipping, after cleaning, a female vulval pad into the external-use agent of 60° C.~80° C. and soaking it for 30~40 minutes, then taking out the pad from the medical liquid and dewatering and drying the pad at a temperature of 50° C.~80° C. to obtain a medical female vulval pad. The medical female vulval pad can also be manufactured using the aforementioned female vulval spraying agent. The preparation method thereof comprises steps of: spraying a female vulval pad after cleaning, with the vulval spraying agent, with the amount per square decimeter of 5~10 ml; drying the pad after the pad is fully saturated and absorbed with the medical liquid; and sterilizing and packaging the dried pad to obtain the medical female vulval pad.

In the development process of the invention, in order to prove the effects of the product according to the present invention that it prevents the repeated gynecological infections, has bacteriostatic, antibacterial, antiviral effects, deodorizes the vagina, and eliminates vulval itching, the inventor of the present invention made researches on medical formulation and repeated clinical practice and drug trial for nearly a decade, and also made bacteriostatic, antibacterial and antiviral experiments aiming at the viruses and bacteria that may infect the ovaries, vagina and vulva, and experiments for effects of deodorizing the vagina and eliminating vulval itching. The results of the above researches and experiments have proved that the product according to the present invention has a very good effect of protecting, cleaning and caring the ovaries, vagina and vulva. The effectiveness of the product according to the present invention is dependent on the degree of preventing the repeated infections, deodorizing the vagina, eliminating vulval itching, cleaning, nourishing and comfort for women, regarded as a standard, the conspicuity is dependent on that a woman does not feel abnormal in her vagina, which is regarded as a standard, and the precaution ability against the diseases is dependent on that a woman does not have abnormal symptoms, regarded as a standard. The inventor of the present invention obtained the following statistical results by interviewing patients who were treated during about a decade:

Statistical magnitude: 300 people (of average age 30~40 years old).

Selection criteria of disease case in the statistics: peculiar smell, vaginal dryness, itching, and inflammation.

Criteria of therapeutic effect: which is evaluated in accordance with Section "gynecology" of 《Diagnostic and Therapeutic Criteria of Diseases in Traditional Chinese Medicine》 (《中医病症诊断疗效标准》).

January 2006 to December 2010, 300 person-times were counted for preventing the repeated infection, deodorizing, eliminating itching, wherein all of the 300 person-times are effective, with the effective percentage of 100%. In the crowd needing care of female reproduction, nursing and cleaning the vulva, each uses on average the product of spraying agent of 30 ml per bottle or pads of 36 pieces per course (6 days). After being cared, 273 people do not feel abnormal in the vagina, vulva, and the conspicuity is more than 90%.

EXAMPLES

Example 1

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 25° C., an extraction pressure of 10 MPa, extraction time of 2 hours, to obtain the propolis extract, the propolis content of which is 1% to 3% of amount of the raw propolis, without heavy metals, and in bright yellow color;

2. preparing zedoary oil, including: directly loading zedoary seeds into a $CO_2$ extraction tank and circularly adding $CO_2$ liquid to perform extraction, with an extraction temperature of 25° C., an extraction pressure of 5 MPa, extraction time of 2 hours, to obtain zedoary oil extract containing plant zedoary ketone ingredient;

3. preparing mint leaf filtrate, including: mixing fresh mint leafs with pure water in a weight ratio of 1:2, breaking into pieces using a colloid mill, then adding into medical ethanol of 0.15 times by weight, soaking for 12 hours, and filtrating with a 200 mesh screen to remove precipitates to obtain the mint leaf filtrate.

(2) Raw materials were prepared according to the following proportion: Propolis extract 300 g, Zedoary oil 600 g, Mint leaf filtrate 5000 g, and Medical ethanol 80 kg, (3). The manufacturing method of the external-use agent comprises the following steps of:

1. dissolving the propolis extract, zedoary extract—zedoary oil and mint leaf filtrate of the above-mentioned amounts, in accordance with requirement of the formula composition, into medical ethanol of 80 Kg and mixing them, and then removing by means of freezing centrifugation, precipitate under the following conditions: a frozen temperature of 0° C.~4° C. and a centrifugal rotation speed of 3500 rpm, the duration of 15 minutes, and then separating the centrifugate by an acoustic membrane separator, discarding residue and retaining supernatant to obtain medical liquid with a molecular weight less than 10000D, then bottling or bagging the medical liquid to obtain the external-use agent.

2. A vulval spraying agent was manufactured using the external agent and purified water being compounded in the proportion of 1:5, or a medical pad was manufactured using the vulval spraying agent, wherein the female vulval pad was sprayed with the vulval spraying agent.

Example 2

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 25° C., an extraction pressure of 10 MPa, and extraction time of 1.5 hours, to obtain the propolis extract, a propolis content of which is 1% to 3% of amount of the raw propolis, without heavy metals, in bright yellow color;

2. preparing zedoary oil, including: directly loading zedoary seeds into a $CO_2$ extraction tank and circularly adding $CO_2$ liquid to perform extraction, with an extraction temperature of 25° C., an extraction pressure of 6 MPa, and extraction time of 1.5 hours, to obtain the zedoary oil extract containing plant zedoary ketone ingredient; and 3. preparing mint leaf filtrate, including: mixing fresh mint leafs with pure water in a weight ratio of 1:3, breaking mechanically into pieces, then adding into medical ethanol of 0.15 times by weight, soaking for 12 hours, and filtrating with a 200 mesh screen to remove precipitates to obtain the mint leaf filtrate.

(2) Raw materials were prepared according to the following proportion: Propolis extract 500 g, Zedoary oil 500 g, Mint leaf filtrate 6000 g, and Medical ethanol 90 kg, (3). The manufacturing method of the external-use agent comprises the following steps of:

1. dissolving the propolis extract, zedoary extract (zedoary oil) and mint leaf filtrate of the above-mentioned amount, in accordance with requirement of the formula composition, into medical ethanol of 90 Kg and mixing, and then remove by means of freezing and centrifugation, precipitates under the following conditions: a frozen temperature of 0° C.~4° C. and a centrifugal rotation speed of 4000 rpm, duration of 20 minutes, and then separating centrifugate by an acoustic membrane separator, discarding residue and retaining the supernatant to obtain medical liquid with a molecular weight less than 10000D, and then bottling or bagging the medical liquid to obtain the external-use agent.

2. A vulval spraying agent was manufactured using the external agent and purified water being compounded in the proportion of 1:8 or a medical pad was manufactured using the vulval spraying agent, wherein the female vulval pad was sprayed with the vulval spraying agent.

Example 3

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 25° C., an extraction pressure of 10 MPa, and extraction time of 2 hours, to obtain the propolis extract, a propolis content of which is 1% of amount of the raw propolis, without heavy metals, in bright yellow color;

2. preparing zedoary oil, including: directly loading zedoary seeds into a $CO_2$ extraction tank and circularly adding $CO_2$ liquid to perform extraction, with an extraction temperature of 25° C., an extraction pressure of 5 MPa, and extraction time of 2 hours, to obtain the zedoary oil extract containing plant zedoary ketone ingredient; and 3. preparing mint leaf filtrate, including: mixing fresh mint leafs with pure water in a weight ratio of 1:2, breaking mechanically into pieces, then adding into medical ethanol of 0.15 times by weight, soaking for 12 hours, and filtrating with a 200 mesh screen to remove precipitates to obtain the mint leaf filtrate.

(2) Raw materials were prepared according to the following proportion:
Propolis extract 300 g,
Zedoary oil 600 g,
Mint leaf filtrate 5000 g, and
Medical ethanol 800 g, (3). The manufacturing method of the external-use agent comprises the following steps of:

1. dissolving the propolis extract, zedoary extract (zedoary oil) and mint leaf filtrate of the above-mentioned amount, in accordance with requirement of the formula composition, into medical ethanol of 800 g and mixing, and then remove by means of freezing and centrifugation, precipitates under the following conditions: a frozen temperature of 0° C. and a centrifugal rotation speed of 3500 rpm, duration of 15 minutes, and then separating centrifugate by an acoustic membrane separator, discarding residue and retaining the supernatant to obtain medical liquid with a molecular weight less than 10000D, and then bottling or bagging the medical liquid to obtain the external-use agent.

2. A vulval spraying agent was manufactured using the external agent and purified water being compounded in the proportion of 1:5 and a medical pad was manufactured using the vulval spraying agent, wherein the female vulval pad was sprayed with the vulval spraying agent.

Example 4

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 25° C., an extraction pressure of 10 MPa, and extraction time of 1.5 hours, to obtain the propolis extract, a propolis content of which is 3% of amount of the raw propolis, without heavy metals, in bright yellow color;

2. preparing zedoary oil, including: directly loading zedoary seeds into a $CO_2$ extraction tank and circularly adding $CO_2$ liquid to perform extraction, with an extraction temperature of 25° C., an extraction pressure of 6 MPa, and extraction time of 1.5 hours, to obtain the zedoary oil extract containing plant zedoary ketone ingredient; and 3. preparing mint leaf filtrate, including: mixing fresh mint leafs with pure water in a weight ratio of 1:3, breaking mechanically into pieces, then adding into medical ethanol of 0.15 times by weight, soaking for 12 hours, and filtrating with a 200 mesh screen to remove precipitates to obtain the mint leaf filtrate.

(2) Raw materials were prepared according to the following proportion: Propolis extract 500 g,
Zedoary oil 500 g,
Mint leaf filtrate 6000 g, and
Medical ethanol 900 g, (3). The manufacturing method of the external-use agent comprises the following steps of:

1. dissolving the propolis extract, zedoary extract (zedoary oil) and mint leaf filtrate of the above-mentioned amount, in accordance with requirement of the formula composition, into medical ethanol of 900 g and mixing, and then remove by means of freezing and centrifugation, precipitates under the following conditions: a frozen temperature of 4° C. and a centrifugal rotation speed of 4000 rpm, duration of 20 minutes, and then separating centrifugate by an acoustic membrane separator, discarding residue and retaining the supernatant to obtain medical liquid with a molecular weight less than 10000D, and then bottling or bagging the medical liquid to obtain the external-use agent.

2. A vulval spraying agent was manufactured using the external agent and purified water being compounded in the proportion of 1:8, and a medical pad was manufactured using the vulval spraying agent, wherein the female vulval pad was sprayed with the vulval spraying agent.

Example 5

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 15° C., an extraction pressure of 8 MPa, and extraction time of 1 hour, to obtain the propolis extract, a propolis content of which is 1% of amount of the raw propolis, without heavy metals, in bright yellow color;

2. preparing zedoary oil, including: directly loading zedoary seeds into a $CO_2$ extraction tank and circularly adding $CO_2$ liquid to perform extraction, with an extraction temperature of 20° C., an extraction pressure of 2 MPa, and extraction time of 1 hour, to obtain the zedoary oil extract containing plant zedoary ketone ingredient; and 3. preparing mint leaf filtrate, including: mixing fresh mint leafs with pure water in a weight ratio of 1:2, breaking mechanically into pieces, then adding into medical ethanol of 0.1 times by weight, soaking for 10 hours, and filtrating with a 200 mesh screen to remove precipitates to obtain the mint leaf filtrate.

(2) Raw materials were prepared according to the following proportion: Propolis extract 0.1 Kg,
Zedoary oil 0.5 Kg, and
Mint leaf filtrate 5 Kg, (3). The manufacturing method of the external-use agent comprises the following steps of:

1. dissolving the propolis extract, zedoary extract (zedoary oil) and mint leaf filtrate of the above-mentioned amount, in accordance with requirement of the formula composition, into medical ethanol of 0.1 times of the active ingredients and mixing, and then remove by means of freezing and centrifugation, precipitates under the following conditions: a frozen temperature of 0° C. and a centrifugal rotation speed of 3000 rpm, duration of 10 minutes, and then separating centrifugate by an acoustic membrane separator, discarding residue and retaining the supernatant to obtain medical liquid with a molecular weight less than 10000D, and then bottling or bagging the medical liquid to obtain the external-use agent.

2. A vulval spraying agent was manufactured using the external agent and purified water being compounded in the proportion of 1:5 or a medical pad was manufactured using the vulval spraying agent, wherein the female vulval pad was sprayed with the vulval spraying agent, with the amount per square decimeter of 5 ml; drying the pad after the pad is fully saturated and absorbed with the medical liquid; and sterilizing and packaging the dried pad to obtain the medical female vulval pad.

Example 6

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 30° C., an extraction pressure of 10 MPa, and extraction time of 2 hours, to obtain the propolis extract, a propolis content of which is 3% of amount of the raw propolis, without heavy metals, in bright yellow color;

2. preparing zedoary oil, including: directly loading zedoary seeds into a $CO_2$ extraction tank and circularly adding $CO_2$ liquid to perform extraction, with an extraction temperature of 30° C., an extraction pressure of 7 MPa, and extraction time of 2 hours, to obtain the zedoary oil extract containing plant zedoary ketone ingredient; and 3. preparing mint leaf filtrate, including: mixing fresh mint leafs with pure water in a weight ratio of 1:3, breaking mechanically into pieces, then adding into medical ethanol of 0.2 times by weight, soaking for 15 hours, and filtrating with a 200 mesh screen to remove precipitates to obtain the mint leaf filtrate.

(2) Raw materials were prepared according to the following proportion:

Propolis extract 1 Kg,
Zedoary oil 1 Kg, and
Mint leaf filtrate 10 Kg, (3). The manufacturing method of the external-use agent comprises the following steps of:

1. dissolving the propolis extract, zedoary extract (zedoary oil) and mint leaf filtrate of the above-mentioned amount, in accordance with requirement of the formula composition, into medical ethanol of 0.3 times of the active ingredients and mixing, and then remove by means of freezing and centrifugation, precipitates under the following conditions: a frozen temperature of 4° C. and a centrifugal rotation speed of 4000 rpm, duration of 20 minutes, and then separating centrifugate by an acoustic membrane separator, discarding residue and retaining the supernatant to obtain medical liquid with a molecular weight less than 10000D, and then bottling or bagging the medical liquid to obtain the external-use agent.

2. A vulval spraying agent was manufactured using the external agent and purified water being compounded in the proportion of 1:10 and a medical pad was manufactured using the vulval spraying agent, wherein the female vulval pad was sprayed with the vulval spraying agent, with the amount per square decimeter of 10 ml; drying the pad after the pad is fully saturated and absorbed with the medical liquid; and sterilizing and packaging the dried pad to obtain the medical female vulval pad.

Example 7

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 20° C., an extraction pressure of 9 MPa, and extraction time of 1.5 hours, to obtain the propolis extract, a propolis content of which is 2% of amount of the raw propolis, without heavy metals, in bright yellow color;

2. preparing zedoary oil, including: directly loading zedoary seeds into a $CO_2$ extraction tank and circularly adding $CO_2$ liquid to perform extraction, with an extraction temperature of 25° C., an extraction pressure of 5 MPa, and extraction time of 1.5 hours, to obtain the zedoary oil extract containing plant zedoary ketone ingredient; and 3. preparing mint leaf filtrate, including: mixing fresh mint leafs with pure water in a weight ratio of 1:2.5, breaking mechanically into pieces, then adding into medical ethanol of 0.15 times by weight, soaking for 12 hours, and filtrating with a 200 mesh screen to remove precipitates to obtain the mint leaf filtrate.

(2) Raw materials were prepared according to the following proportion: Propolis extract 0.5 Kg, Zedoary oil 0.7 Kg, and
Mint leaf filtrate 7 Kg, (3). The manufacturing method of the external-use agent comprises the following steps of:

1. dissolving the propolis extract, zedoary extract (zedoary oil) and mint leaf filtrate of the above-mentioned amount, in accordance with requirement of the formula composition, into medical ethanol of 0.2 times of the active ingredients and mixing, and then remove by means of freezing and centrifugation, precipitates under the following conditions: a frozen temperature of 2° C. and a centrifugal rotation speed of 3500 rpm, duration of 15 minutes, and then separating centrifugate by an acoustic membrane separator, discarding residue and retaining the supernatant to obtain medical liquid with a molecular weight less than 10000D, and then bottling or bagging the medical liquid to obtain the external-use agent.

2. The vulval spraying agent is manufactured using the external agent and purified water being compounded in the proportion of 1:7. And female medical vulval pads were prepared by the preparation method comprising steps of: dipping, after cleaning, a female vulval pad into the external-use agent of 30° C. and soaking it for 30 minutes, then taking out the pad from the medical liquid and dewatering and drying the pad at a temperature of 50° C. to obtain a medical female vulval pads.

Example 8

(1). Medical raw materials were prepared in the following steps of:

1. preparing propolis extract, including: loading raw propolis into a $CO_2$ extraction tank and circularly adding $CO_2$ liquid to perform extraction, with an extraction temperature of 28° C., an extraction pressure of 10 MPa, and extraction time of 2 hours, to obtain the propolis extract, a propolis content of which is 3% of amount of the raw propolis, without heavy metals, in bright yellow color;

2. preparing zedoary oil, including: directly loading zedoary seeds into a $CO_2$ extraction tank and circularly adding $CO_2$ liquid to perform extraction, with an extraction temperature of 28° C., an extraction pressure of 6 MPa, and extraction time of 2 hours, to obtain the zedoary oil extract containing plant zedoary ketone ingredient; and 3. preparing mint leaf filtrate, including: mixing fresh mint leafs with pure water in a weight ratio of 1:3, breaking mechanically into pieces, then adding into medical ethanol of 0.2 times by weight, soaking for 14 hours, and filtrating with a 200 mesh screen to remove precipitates to obtain the mint leaf filtrate.

(2) Raw materials were prepared according to the following proportion:

Propolis extract 0.9 Kg,
Zedoary oil 0.9 Kg, and
Mint leaf filtrate 9 Kg, (3). The manufacturing method of the external-use agent comprises the following steps of:

1. dissolving the propolis extract, zedoary extract (zedoary oil) and mint leaf filtrate of the above-mentioned amount, in accordance with requirement of the formula composition, into medical ethanol of 0.25 times of the active ingredients and mixing, and then remove by means of freezing and centrifugation, precipitates under the following conditions: a frozen temperature of 3° C. and a centrifugal rotation speed of 3800 rpm, duration of 18 minutes, and then separating centrifugate by an acoustic membrane separator, discarding residue and retaining the supernatant to obtain medical liquid with a molecular weight less than 10000D, and then bottling or bagging the medical liquid to obtain the external-use agent.

2. The vulval spraying agent is manufactured using the external agent and purified water being compounded in the proportion of 1:9. And female medical vulval pads were prepared by the preparation method comprising steps of: dipping, after cleaning, a female vulval pad into the external-use agent of 50° C. and soaking it for 40 minutes, then taking out the pad from the medical liquid and dewatering and drying the pad at a temperature of 80° C. to obtain a medical female vulval pads.

The invention claimed is:

1. An external-use composition effective for cleaning and caring for ovaries, vagina and vulva, wherein the external-use composition effectively inhibits or prevents repeated infection of the ovaries, the composition comprising therapeutically effective amounts of the following, by parts by weight of the composition:
   propolis extract in an amount of 1 to 10 parts by weight, zedoary oil in an amount of 5 to 10 parts by weight, and mint leaf filtrate in an amount of 50 to 100 parts by weight,
   wherein the external-use composition is a medical liquid composition prepared by a method comprising:
   preparing the propolis extract, including: loading raw propolis into a $CO_2$ extraction tank and circularly adding $CO_2$ liquid to perform extraction with an extraction temperature of 15 to 30° C., an extraction pressure of 8 to 10 MPa, and extraction time of 1 to 2 hours, to obtain the propolis extract, a propolis content of which is 1% to 3% of amount of the raw propolis;
   preparing the zedoary oil, including: directly loading zedoary seeds into a $CO_2$ extraction tank and circularly adding $CO_2$ liquid to perform extraction with an extraction temperature of 20 to 30° C., an extraction pressure of 2 to 7 MPa, and extraction time of 1 to 2 hours, to obtain zedoary oil extract containing a plant zedoary ketone ingredient;
   preparing the mint leaf filtrate, including: mixing fresh mint leafs with pure water in a weight ratio of 1:2 to 1:3, breaking the fresh mint leafs in water mechanically into pieces, adding medical ethanol of 0.1 to 0.2 times by weight, soaking for 10 to 15 hours, and filtrating with a 200 mesh screen to remove precipitates to obtain the mint leaf filtrate;
   dissolving the propolis extract, the zedoary oil extract and the mint leaf filtrate, in accordance with requirements of the formula composition, into medical ethanol of 0.1 to 0.3 times by weight of the active ingredients, and mixing them, and then removing by freezing and centrifugation, precipitates under the following conditions: at a frozen temperature of 0° C. to 4° C. and at a centrifugal rotation speed of 3000 rpm to 4000 rpm, for a duration of 10 to 20 minutes, and then separating centrifugate by an acoustic membrane separator to obtain a medical liquid with a molecular weight less than 10000D,
   obtaining the external-use composition, and
   optionally bottling or bagging the external-use composition.

2. A product for cleaning and caring for ovaries, vagina and vulva, comprising the external-use composition prepared in accordance with claim 1, wherein the product is a vulval spraying agent.

3. The product for cleaning and caring for ovaries, vagina and vulva, according to claim 2, wherein the vulval spraying agent is formed by compounding the external-use composition and purified water or alcohol at a proportion of 1:5 to 1:10.

4. A medical female vulval pad comprising the product for cleaning and caring for ovaries, vagina and vulva according to claim 2, wherein a method for preparing the medical female vulval pad comprises steps of: spraying, after cleaning, a female vulval pad with the vulval spraying agent with an amount of 5 to 10 ml per square decimeter; drying the pad after the pad is fully saturated and absorbed with the medical liquid; and sterilizing and packaging the dried pad to obtain the medical female vulval pad.

5. A product for cleaning and caring for ovaries, vagina and vulva, comprising the external-use composition prepared in accordance with claim 1, wherein the product is a medical female vulval pad, and a method for preparing the medical female vulval pad comprises steps of: dipping, after cleaning, the medical female vulval pad into the external-use composition at 60° C. to 80° C. and soaking for 30 to 40 minutes, then taking the medical female vulval pad out from the medical liquid and dewatering and drying the medical female vulval pad at a temperature of 50° C. to 80° C. to obtain the medical female vulval pad.

* * * * *